United States Patent [19]

Broutman et al.

[11] 4,350,495
[45] Sep. 21, 1982

[54] CHEMILUMINESCENCE APPARATUS AND METHOD FOR DETERMINING THE OXIDATIVE STABILITY OF POLYMERS

[76] Inventors: Lawrence J. Broutman, 1037 Edgebrook La., Glencoe, Ill. 60022; Boris Rozhansky, 4902-B W. Carol, Skokie, Ill. 60077; Lev Zlatkevich, 1310 Lunt, Apt. 105, Chicago, Ill. 60626

[21] Appl. No.: 214,231

[22] Filed: Dec. 8, 1980

[51] Int. Cl.³ .................. G01N 21/76; G01N 33/44
[52] U.S. Cl. ......................... 23/230 PC; 23/230 M; 422/52; 422/78
[58] Field of Search .............. 23/230 PC, 230 M; 422/52, 78

[56] References Cited

U.S. PATENT DOCUMENTS

| | | | |
|---|---|---|---|
| 4,018,562 | 4/1977 | Parks et al. | 23/230 M |
| 4,049,383 | 9/1977 | Burton et al. | 422/52 X |
| 4,193,963 | 3/1980 | Bruening et al. | 422/52 X |

Primary Examiner—Ronald E. Serwin
Attorney, Agent, or Firm—McDougall, Hersh & Scott

[57] ABSTRACT

A chemiluminescence apparatus and method for determining polymer stability by measuring the intensity of the light emitted during thermal oxidation. The apparatus described in the invention measures the light intensity vs. time from polymers in an oxidative atmosphere. On the basis of this information, important parameters such as induction time and oxidation rate can be obtained. The apparatus has the advantage of simultaneous multi-sample analysis and the mathematical approach enables data computerization.

19 Claims, 8 Drawing Figures

I — INDUCTION PERIOD
II — AUTO CATALYTIC STAGE
III — LUMINESCENCE DECAY

CHEMILUMINESCENCE APPARATUS AND METHOD FOR DETERMINING THE OXIDATIVE STABILITY OF POLYMERS

This invention relates to a method for determining polymer stability by measurement of the intensity of light emitted during thermal oxidation and it relates to an apparatus for use in same.

BACKGROUND OF THE INVENTION

It is often desirable for polymer producers, end-use manufacturers, additive suppliers, academicians, and others to establish quality control tests concerning antioxidant concentration or oxidative stability. Numerous techniques have been developed over the years to study the oxidative stability of polymers. Among various methods, chemiluminescence accompanying the thermal oxidation of polymers has been referred to by several authors (1–7). It was pointed out that the intensity of emitted light could be a convenient criterion for the estimation of thermal oxidative stability of polymers. The relationship $$G_t = K[ROOH]_t \qquad (1)$$

has been proposed where $G_t$ is time dependent light intensity, K is a constant and $[ROOH]_t$ is hydroperoxide concentration (4).

In spite of the fact that the first publications concerning the possibility of using the chemiluminescence technique as the method for evaluating polymer thermal oxidative stability appeared about 20 years ago, no commercial installation of this kind has so far been offered. There are several reasons explaining this discrepancy:

1. Chemiluminescence technique is still largely a matter of discovering conditions under which the light emission relates to the properties of interest.
2. The treatment of chemiluminescence results was based mainly on the comparison of maximum light intensities emitted by different samples and much additional important information has been missed.
3. The chemiluminescence test requires many hours, especially when applied for the analysis of highly stabilized polymer systems. Thus, the productivity of the instruments used was low and could not satisfy the requirements.

It would therefore be desirable to have a method for the evaluation of chemiluminescence results which will provide various information (induction time, oxidation rate) concerning the thermal oxidative stability. It would also be advantageous to provide an instrument which would be able to analyze numerous polymer samples simultaneously.

Accordingly, it is an object of the present invention to provide a new chemiluminescence instrument and method having both the above mentioned features.

DESCRIPTION OF THE DRAWINGS

These and other objects and advantages of this invention will hereinafter appear, and for purposes of illustration, but not of limitation, an embodiment of the apparatus employed in the practice of this invention is shown in the following drawings in which.

DESCRIPTION OF THE APPARATUS

Figure 1:
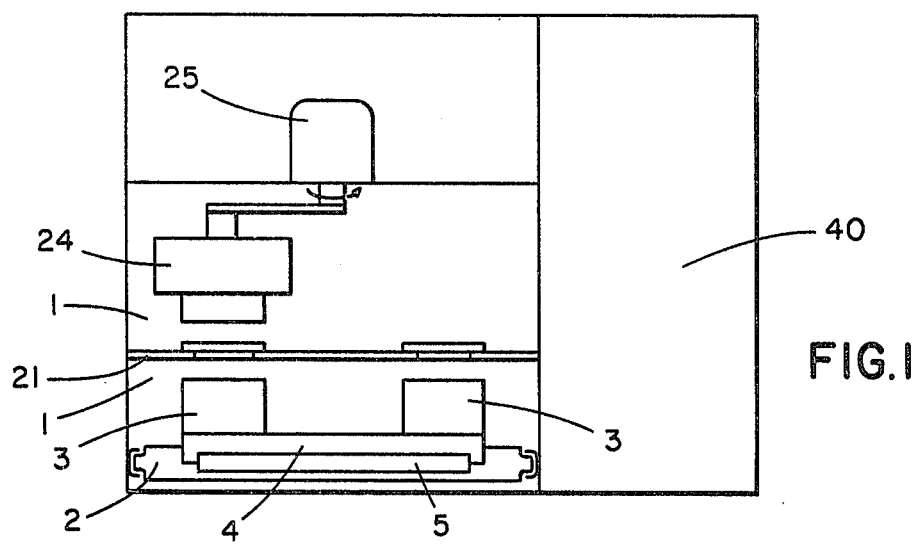
FIGS. 1, 2 and 3 are schematic diagrams of various modifications in an apparatus embodying the features of this invention.
Figure 2:
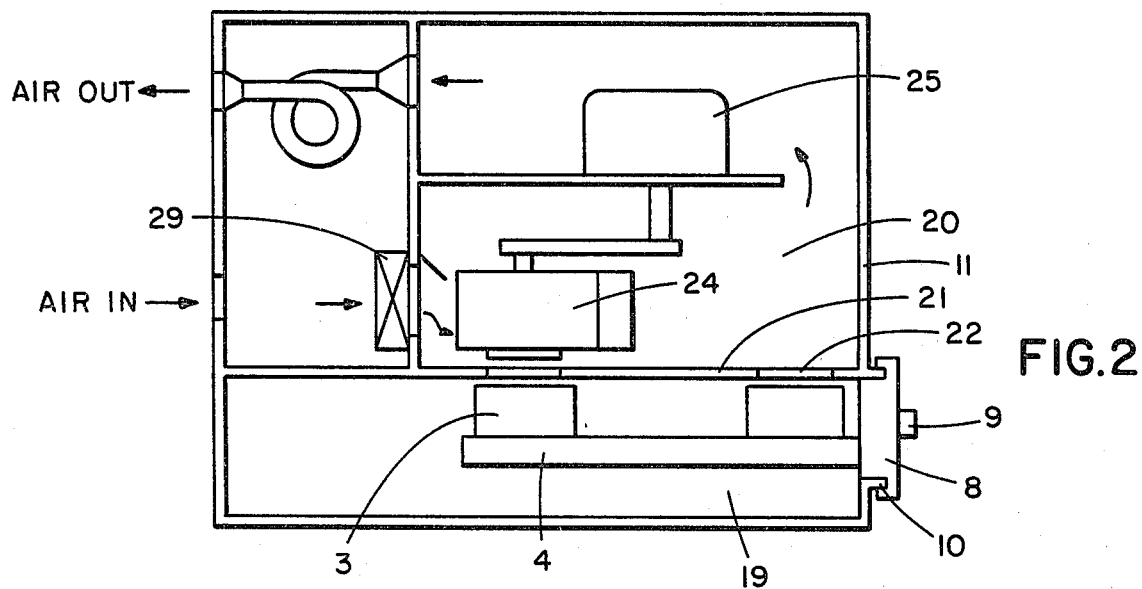
Figure 3:
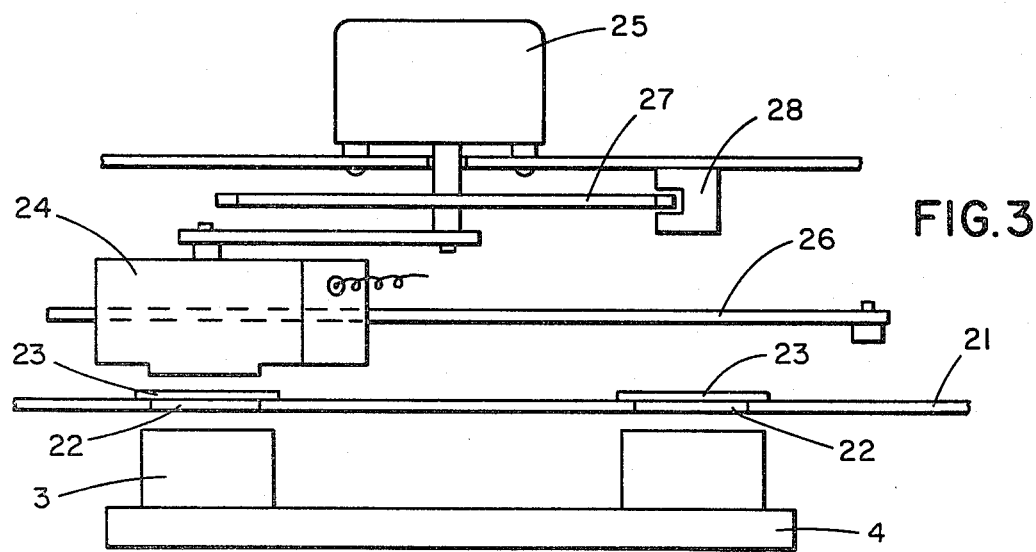
Figure 4:
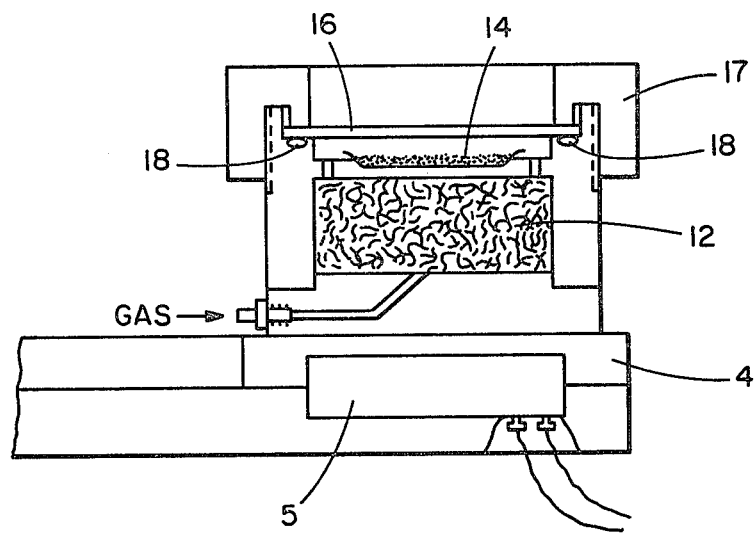
FIG. 4 is a diagrammatic sectional elevational view of a cell used in the apparatus of FIGS. 1–3.
Figure 5:
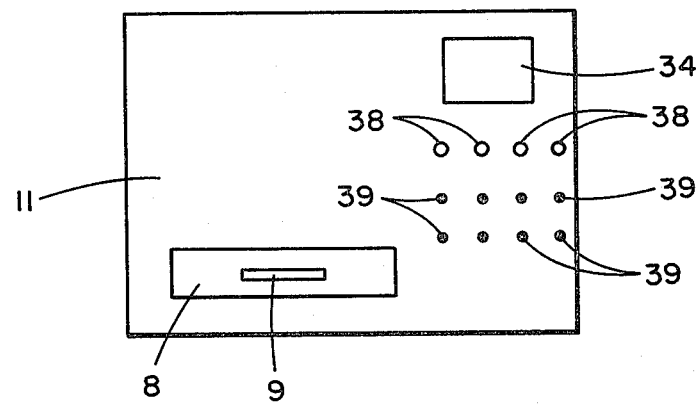
FIG. 5 is an elevational view from the front side of the apparatus of this invention.
Figure 6:
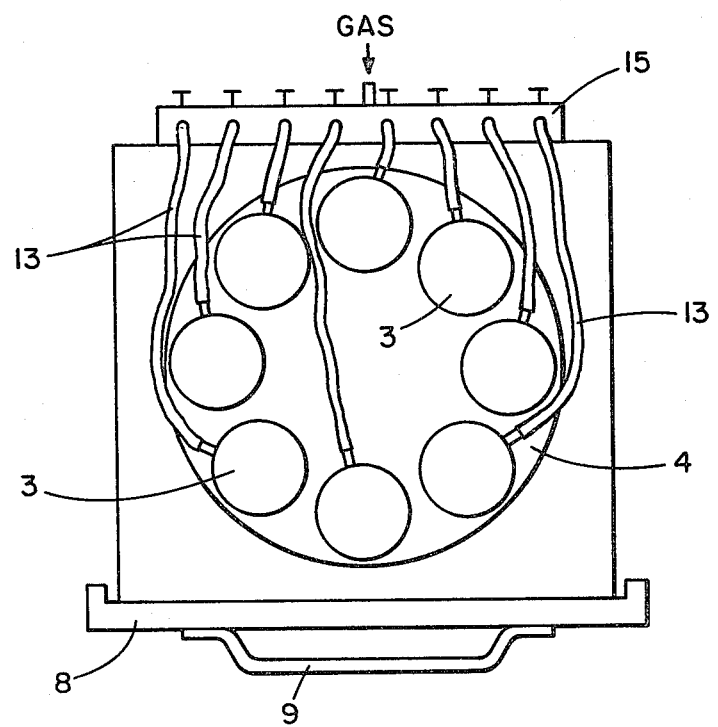
FIG. 6 is a schematic diagram showing the gas flow to the multiple cells of the apparatus of FIGS. 1–3.
Figure 7:
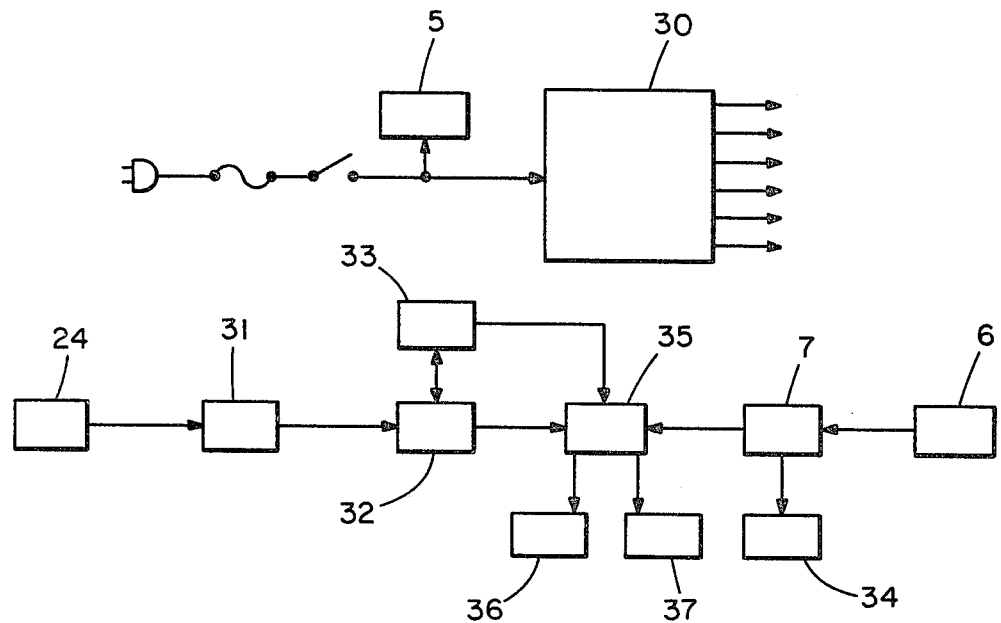
FIG. 7 is an electrical diagram showing the electrical circuit.

The apparatus of the invention comprises a dark chamber 1 with a sliding stage 2 which holds numerous individual test cells 3. The test cells are maintained on a metal support plate 4 which provides even temperature distribution to the cells. A heater 5, such as an electrical resistance heater, is placed under the metal plate and thermocouples 6 and a temperature controller 7 are used in the conventional manner to maintain the desired temperature. The sliding stage has on its exterior side a plate 8 with a handle 9 and can be moved in and out of the dark chamber. The plate edges have a complicated shape and when the sliding stage is in "in" position, the plate tightly fits a frame 10 on the front panel 11 of the instrument. This prevents light penetration from the outside to the dark chamber 1 during the experiments.

The test cells 3 have a unique construction contributing to the warm up of the gas before reaching the test samples. Each cell contains metal shavings 12 which have a large surface area for heat exchange. The gas flow in line 13 to each sample 14 is evenly distributed by a manifold 15 with individual flow adjustment. Each test cell 3 is covered by a glass cover 16 to prevent cross contamination. Glass covers also restrict reaction volume of each cell and promote fast replacement of one gas by another. The test cell 3 construction provides the opportunity to carry out the experiments not only under gas flow but also under gas pressure. In order to pressurize gas inside of the cell up to several atmospheres, a metal cap 17 with a teflon gasket 18 is placed above the covering glass 16 and tightened to the cell. The lower part 19 of the dark chamber is separated from its upper part 20 by a metal plate 21 with a number of holes 22 equal to the number of test cells. Each hole in the separating plate is covered by a glass window 23. When the sliding stage is in "in" position, each of the holes 22 in the separating plate 21 is strictly above one of the test cells 3. The light emitted by the samples placed in the test cells is sequentially measured by a rotating photomultiplier 24 placed in the upper part of the dark chamber. The rotation of the photomultiplier is provided by an electric motor 25 and unique holding arm 26 the construction of which avoids the need for sliding contacts. The electrical motor also rotates a disk 27 which sequentially activates micro switches 28 for determining the location of the photomultiplier. The light output is synchronously recorded with the sample position. This assures sequential sampling of light intensity from multi-sample apparatus. In order to avoid the photomultiplier overheating during the experiments a fan 29 is placed in the upper part 20 of the dark chamber. The fan provides constant outside air circulation through the upper part of the dark chamber. Electronic part of the apparatus consists of a power supply 30, the photomultiplier current amplifier 31, a signal conditioning circuit 32, a sequential circuit 33, a temperature controller with a digital display 34, a computer 35 with a printer 36, and a display 37, control knobs 38 and pilot lights 39. All electronic equipment is located in a separate compartment 40.

TYPICAL OPERATION CONDITIONS AND CURVES

DESCRIPTION OF THE METHOD

Figure 8:
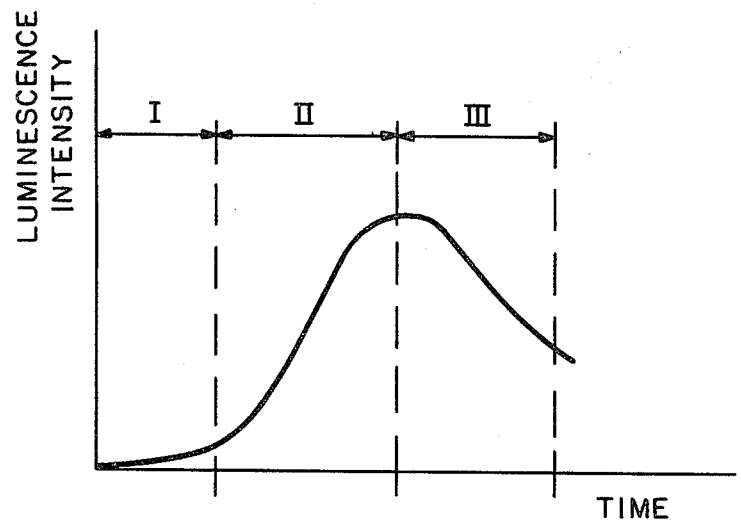
FIG. 8 is a typical curve of light intensity vs. time for chemoluminescence produced by auto-oxidation of a polymer in accordance with the practice of this invention.

Each of the samples studied is placed in a separate test cell 3 and covered by the glass cover 16 at room temperature under a nitrogen atmosphere. The heater 5 is then turned on and the samples heated up to a desired temperature. In the case of polypropylene, the sample is heated to a temperature 5°–30° C. below its melting point, such as to a temperature of 150° C. The nitrogen supply is then replaced by oxygen and the experiment starts either under oxygen flow or under oxygen pressure. In the latter case, the covering cap 17 should be tightened to the cell. A typical light intensity vs. time curve for the chemiluminescence produced by auto-oxidation of a polymer (normally made at constant sample temperature) is presented in FIG. 8. There is an induction period during which the light intensity is low and constant, oxidation is slight and build-up of peroxides or hydro-peroxides is slow. This induction period will vary in length depending on the chemical structure of the polymer, the presence of impurities and the temperature of oxidation. Following the induction period there is an autocatalytic stage in which the peroxides catalyze further oxidation. The rate of this first order chemical reaction at any given temperature is influenced by impurities arising from different methods of polymer manufacture. The induction and acceleration periods are not separate phenomenon, but parts of a typical autocatalytic reaction. The light intensity next reaches the highest level (peak peroxide concentration). Finally, there is a period of light decay (a deceleration of the rate of oxidation).

The shape of the chemiluminescence curve provides data from which significant information can be derived.

In the simplest case of the autocatalytic reaction of first order we have:

$$\frac{d(B)}{dt} = K[A][B] \tag{2}$$

where [A] is a polymer and [B] is hydroperoxide concentrations respectively. Designating the increase in [B] during the oxidation as $X (X = [B] - [B]_o)$ and considering that the increase in [B] is equal to the decrease in [A], $([B] - [B]_o = [A]_o - [A])$ $$\frac{dX}{dt} = K([A]_o - X)([B]_o + X) \tag{3}$$

where $[A]_o$ and $[B]_o$ are the initial polymer and peroxide concentrations, respectively.

Integration of equation (3) gives:

$$K([A]_o + [B]_o)t = \ln\left(\frac{[B]_o + X}{[A]_o - X} \cdot \frac{[A]_o}{[B]_o}\right) \tag{4}$$

or $$X = \frac{[B]_o(e^{K([A]_o + [B]_o)t} - 1)}{1 + \frac{[B]_o}{[A]_o} e^{K([A]_o + [B]_o)t}} \tag{5}$$

In the above equations, parameter K is proportional to oxidation rate, whereas parameter $[B]_o$ is reciprocally proportional to induction time.

Since the chemiluminescence emission intensity is proportional to hydroperoxide concentration (see equation (1)), $$G_t = C([B] - [B]_o) = CX \tag{6}$$

When the chemiluminescence intensity levels off, all polymer is oxidized $$G_{max} = C[A]_o \tag{7}$$

Two cases should be considered:
1. $[B]_o << [A]_o$ (long induction time)

Equation (4) can be rewritten $$K[A]_o t = \ln \frac{[A]_o X}{([A]_o - X)[B]_o} \tag{8}$$

Substituting $[A]_o$ and X from (6) and (7) into (8)

$$\ln \frac{G_t}{G_{max} - G_t} = \ln \frac{C[B]_o}{G_{max}} + K \frac{G_{max}}{C} t \tag{9}$$

Equation (9) provides a good method of estimating $C[B]_o$ and K/C values. A plot of $\ln G_t/G_{max} - G_t$ against t has slope $(K/C)G_{max}$ and intercept $\ln (C[B]_o/G_{max})$ 2. $[B]_o </< [A]_o$ (short induction time)

When $[B]_o$ is not essentially smaller than $[A]_o$, it can be found if one knows $X_1$ and $X_2$ values corresponding to two moments of time $t_1$ and $t_2$.

$$X_1 = \frac{G_1}{C} = \frac{[B]_o \left[ e^{K(\frac{G_{max}}{C} + [B]_o)t_1} - 1 \right]}{1 + \frac{[B]_o C}{G_{max}} e^{K(\frac{G_{max}}{C} + [B]_o)t_1}} \tag{10}$$

Choosing $t_2 = 2t_1$ $$\frac{G_2}{C} = \frac{[B]_o \left[ e^{K(\frac{G_{max}}{C} + [B]_o)2t_1} - 1 \right]}{1 + \frac{[B]_o C}{G_{max}} e^{K(\frac{G_{max}}{C} + [B]_o)2t_1}} \tag{11}$$

Introducing parameter Z $$Z = e^{\frac{KG_{max}}{C}(1 + \frac{[B]_o C}{G_{max}})t_1}$$

one obtains $$\frac{G_1}{C} = \frac{[B]_o(Z - 1)}{1 + \frac{[B]_o C}{G_{max}} Z} \tag{12}$$

and $$\frac{G_2}{C} = \frac{[B]_o(Z^2 - 1)}{1 + \frac{[B]_oC}{G_{max}}Z^2} \quad (13)$$

From (12) and (13)

$$\frac{C[B]_o}{G_{max}} = \frac{G_1/G_{max}}{Z - 1 - Z\frac{G_1}{G_{max}}} = \frac{G_2/G_{max}}{Z^2 - 1 - Z^2\frac{G_2}{G_{max}}} \quad (14)$$

or $$Z^2 \frac{G_1}{G_{max}}\left(1 - \frac{G_2}{G_{max}}\right) - Z\frac{G_2}{G_{max}}\left(1 - \frac{G_1}{G_{max}}\right) + \quad (15)$$

$$\left(\frac{G_2}{G_{max}} - \frac{G_1}{G_{max}}\right) = 0$$

The solution of equation (15) is $$Z = \frac{\frac{G_2}{G_{max}}\left(1 - \frac{G_1}{G_{max}}\right) \pm \sqrt{\frac{G_2^2}{G_{max}^2}\left(1 - \frac{G_1}{G_{max}}\right)^2 - 4\frac{G_1}{G_{max}}\left(1 - \frac{G_2}{G_{max}}\right)\left(\frac{G_2}{G_{max}} - \frac{G_1}{G_{max}}\right)}}{2\frac{G_1}{G_{max}}\left(1 - \frac{G_2}{G_{max}}\right)} \quad (16)$$

$$\begin{cases} C[B]_o = \dfrac{G_1}{Z - 1 - \dfrac{G_1}{G_{max}}Z} \\ \dfrac{K}{C} = \dfrac{\ln Z}{G_{max}\, t_1\left(1 + \dfrac{G_1}{G_{max}}/Z - 1 - Z\dfrac{G_1}{G_{max}}\right)} \end{cases}$$

$C[B]_o$ and $K/C$ values can be either calculated from a chart of a multichannel recorder or computerized by a computer with a printout device.

REFERENCES

1. G. E. Ashby, J. Polym. Sci., Vol. L, 99–106, 1961.
2. N. S. Allen and J. F. McKeller, Polymer, 18, 968, 1977.
3. L. Matisova, European Polymer J., 14, 1033, 1978.
4. S. S. Stivala and L. Reich, J. Polym. Sci., A3, Y299, 1965.
5. M. P. Schard and C. A. Russell, J. App. Polym. Sci., 8, 985, 1964.
6. L. Matisova, J. Polym. Sci., Symposium, No. 57, 181, 1976.
7. L. Reich and S. S. Stivala, J. Polym. Sci., A3, Y299, 1965.

I claim:

1. A method of determining chemical processes accompanied by chemiluminescence and oxidative stability of a polymer by measuring the chemiluminescence produced by auto-oxidation of the polymer comprising heating the polymer in a cell to elevated temperature, exposing the polymer to oxygen for thermal oxidation of the polymer, recording the light intensity versus time given off by the polymer during oxidation while at relatively constant temperature from which the chemiluminescence can be determined by auto oxidation of the polymer.

2. The method as claimed in claim 1 in which the polymer in the cell is maintained under inert atmosphere until the inert atmosphere is replaced by an oxidative atmosphere.

3. The method as claimed in claim 1 in which the polymer is exposed to an oxidative atmosphere under flow of an oxygen containing gas.

4. Apparatus for determining polymer stability by measurement of the intensity of light emitted from the polymer during thermal oxidation comprising
   a dark chamber,
   a support for the polymer,
   means for moving the support into and out of the dark chamber,
   means for heating the polymer while in the dark chamber,
   means for exposing the polymer to an oxidative atmosphere containing gas while at elevated temperature within the chamber for thermal oxidation of the polymer
   and means for measuring the intensity of light emitted from the polymer during auto-oxidation.

5. Apparatus as claimed in claim 4 which includes means for maintaining an inert atmosphere within the dark chamber.

6. Apparatus as claimed in claim 4 in which the support comprises a metal plate.

7. Apparatus as claimed in claim 6 in which the means for heating the polymer while in the dark chamber comprises heaters adjacent the bottom side of the metal plate.

8. Apparatus as claimed in claim 4 which includes metal shavings for elevating the temperature of the oxygen containing gas before reaching the polymer.

9. Apparatus as claimed in claim 4 in which the support is in the form of a sliding stage which supports a plurality of test cells.

10. Apparatus as claimed in claim 9 which includes a glass cover for each test cell to prevent cross contamination.

11. Apparatus as claimed in claim 9 which includes enclosures for each test cell to restrict reaction volume and enhance replacement of one gas by another.

12. Apparatus as claimed in claim 9 which includes a means for enclosing the test polymer for exposure of the polymer to oxygen under pressure.

13. Apparatus as claimed in claim 9 which includes a partitioning plate which subdivides the dark chamber into an upper portion and a lower portion, said partitioning plate having openings which overlie the test cell when in position of use.

14. Apparatus as claimed in claim 13 which includes transparent windows to cover the openings in the partitioning plate for visual access to the test cells underlying the openings.

15. Apparatus as claimed in claim 9 which includes a photomultiplier and means for movement of the photomultiplier for sequential measurement of the light intensity being emitted from the test cells and a power source connected to the photomultiplier for supply of operative voltage thereto.

16. Apparatus as claimed in claim 15 which includes means for circulating cooling gas through the upper portion of the dark chamber to prevent overheating of the photomultiplier.

17. The method as claimed in claim 1 in which the polymer is exposed to oxygen for auto oxidation by oxygen under pressure.

18. The method as claimed in claim 1 in which the polymer is heated to a temperature 5°–30° C. below its melting point temperature.

19. The method as claimed in claim 18 in which the polymer is maintained at a temperature 5°–30° C. below its melting point during the auto oxidation period recorded.

* * * * *